(12) United States Patent
Fukuda

(10) Patent No.: US 6,917,828 B2
(45) Date of Patent: Jul. 12, 2005

(54) AUTOMATIC INJECTION DEVICE

(75) Inventor: Takashi Fukuda, Bunkyo-ku (JP)

(73) Assignee: Nemoto Kyorindo Co., Ltd., Tokyo (JP)

( * ) Notice: Subject to any disclaimer, the term of this patent is extended or adjusted under 35 U.S.C. 154(b) by 334 days.

(21) Appl. No.: 09/963,427

(22) Filed: Sep. 27, 2001

(65) Prior Publication Data

US 2002/0049415 A1 Apr. 25, 2002

(30) Foreign Application Priority Data

Oct. 3, 2000 (JP) ........................................ 2000-303717

(51) Int. Cl.[7] .............................................. A61B 6/00
(52) U.S. Cl. ........................................ 600/432; 604/28
(58) Field of Search ....................... 600/432, 4; 604/28, 604/191, 82, 523, 90; 128/916

(56) References Cited

U.S. PATENT DOCUMENTS

| | | | | |
|---|---|---|---|---|
| 4,044,757 A | * | 8/1977 | McWhorter et al. | 600/432 |
| 4,867,742 A | * | 9/1989 | Calderon | 604/28 |
| 5,078,691 A | * | 1/1992 | Hamacher | 604/191 |
| 5,236,417 A | * | 8/1993 | Wallis | 604/82 |
| 5,236,424 A | * | 8/1993 | Imran | 604/523 |
| 5,298,023 A | * | 3/1994 | Haber et al. | 604/90 |
| 5,472,403 A | * | 12/1995 | Cornacchia et al. | 600/4 |

FOREIGN PATENT DOCUMENTS

| | | |
|---|---|---|
| EP | 0 402 553 | 12/1990 |
| GB | 1 391 575 | 4/1975 |

* cited by examiner

*Primary Examiner*—Ali Imam
(74) *Attorney, Agent, or Firm*—Oblon, Spivak, McClelland, Maier & Neustadt, P.C.

(57) ABSTRACT

An automatic injection device has piston holders holding cylinder pistons and plural systems of heads having a drive mechanism for moving the piston holders forward and backward so that the device can hold a plurality of syringes and operates injection or suction in each syringe independently. This device also has a mechanism for prohibiting the backward-moving of the piston holder of a second head when the piston holder of a first head is in a forward-moving state and the piston holder of the second head is in a stopped state. This structure effectively prevents liquid from being undesirably mixed and the injection amount thereof from becoming less accurate.

16 Claims, 9 Drawing Sheets

AUTOMATIC INJECTION DEVICE

BACKGROUND OF THE INVENTION

1. Field of the Invention

The present invention relates to a contrast medium injection device used for X-ray CT image diagnosis, MRI image diagnosis and the like.

2. Description of the Related Art

A contrast medium is used for the diagnosis of X-ray CT (computed tomography) images, MRI, angio-images (angiographic images) and the like. The contrast medium is a liquid having high viscosity and the injection thereof by means of a manual power takes a lot of time and labor so that in recent years automatic contrast medium injection devices have come to be used.

An automatic injection device 100 of FIG. 8 is an example of such devices, and since it can be mounted with two syringes, it is referred to as a double-head type. FIG. 9 shows a typical mechanism of the automatic injection device. A syringe 1a for the contrast medium is set at the side of a head A, a syringe 1b for a physiological saline solution is set at the side of a head B, and a Y-shaped tube 2 is connected to the tips of the two syringes. A catheter is connected to the tip of the Y-shaped tube and can be injected with the contrast medium and the physiological saline solution.

The physiological saline solution is used mainly for flushing inside the tube in order to prevent blood from coagulating inside the catheter and the tube after the contrast medium was injected. It is also used for the purpose of diluting the contrast medium.

As for the essential action of the device, injection of a required amount of the contrast medium is performed by forwarding a syringe piston of the head A while a syringe piston at the head B stopped, and then after the side of the head A is stopped, the side of the head B is moved forward to perform flushing with the physiological saline solution. In order to dilute the contrast medium, both cylinder pistons of the head A and the head B are moved forward so as to mix the liquid of both heads A and B in the Y-shaped tube (i.e. three way-branched tube).

In the automatic injection device of FIGS. 8 and 9, rotations of motors 4a, 4b at the sides of the head A and the head B, respectively, are transferred to motor gears 6a, 6b via gear heads 5a, 5b, and transferred to screw gears 7a, 7b linked to ball screws 8a, 8b by being reduced to a predetermined gear ratio to rotate the ball screws 8a, 8b. Furthermore, the rotation is converted into a linear movement by ball nut units 9a, 9b which are engaged with the ball screws 8a, 8b so that piston holders 3a, 3b which hold the syringe pistons are allowed to move forward or backward.

However, since the contrast medium has high viscosity, and high pressure is necessary for the injection, specifically when the contrast medium is injected, the high pressure is also transferred to the side of the head B via the Y-shaped tube. Therefore, in the case of the device using a mechanism having an extremely small frictional factor such as that of the ball screw, there was the possibility that the syringe piston at the side of the head B is pushed and forced to move backward by high pressure and the contrast medium is sucked by the head B.

For this reason, an idea can be conceived that a valve is provided between the Y branch of the Y-shaped tube and the head B so that the valve is closed when the syringe piston at the head B is in a stopped state. However, when a manually operable valve is used for this purpose, the switching operation of the valves is complicated and the switching is sometimes forgotten. Although it is possible to perform the switching of the valves automatically and electrically, it is not preferable to provide a drive unit of such a switching in the midway through a substantially soft and light tube because the balance of the device configuration become worse.

On the other hand, if a one-way valve is used, the device can be made simple and compact, but the backward-moving action of the syringe piston cannot be performed. Although an idea can be also conceived that a pressure in the forward direction is applied to the syringe piston at the head B so as to resist the pressure from the side of the head A when the syringe piston at the head B is in a stopped state, the axis of rotation of the motor continues to be in a stopped state while electricity is being supplied to the motor, and there arises a problem of the seizing of the motor.

SUMMARY OF THE INVENTION

The present invention has been devised in order to solve such a problem and it is an object of the present invention to provide an automatic injection device mountable with a plurality of syringes, in which when at least one head is in a state of injection and at least one head is in a stopped state, the backward-moving of the cylinder piston of the stopped head is prevented so as to prevent liquid from undesirably being mixed and the amount thereof from unreliably being injected.

The present invention is directed to an automatic injection device comprising piston holders holding cylinder pistons and plural systems of heads having a drive mechanism for moving the piston holders forward and backward, whereby the device can hold a plurality of syringes and operates injection or suction in each syringe independently; said device comprising a backward-moving prohibition mechanism for prohibiting the backward-moving of the piston holder of a second head when the piston holder of a first head is in a forward-moving state and the piston holder of the second head is in a stopped state.

According to the present invention, when the syringe piston mounted at the second head is in a stopped state, even if the piston holder is moved forward for the injection of a chemical solution in the syringe at a the first head, the backward-moving of the syringe piston at the second head can be prevented. Therefore the chemical solution in the syringe of the first head does not flow into the syringe of the second head, thereby the mixture of the chemical solution can effectively prevented.

In the present invention, a "head" refers to a system of a syringe holding and driving mechanism which can hold a syringe and allow a syringe piston to move forward and backward in order to inject and suck the chemical solution and the like. The number of heads provided for the automatic injection device of the present invention is more than two and, though a plurality of heads may form an independent body of equipment, it is preferable that they are usually assembled into the same body of equipment. From among a plurality of heads, a head which allows preventing the unnecessary backward-moving of the piston holder is taken as a second head, and a head which causes the backward-moving of the piston holder of the second head is taken as a first head. Hence, in the case of a multi-head with the number of heads being more than three, a plurality of heads corresponding to the above described first or second head may sometimes exist. Moreover, there are some cases where one head can be the first head and yet the second head as well. That is, in relation to other heads, a certain head may be sometimes a first head during a certain action and may be a second head during a different action.

In a normal application, a double head type having two heads is used quite often and, in this case, the first head is most commonly used for injecting the contrast medium and the second head for injecting the physiological saline solution.

In case that this device is a multi-head type that holds a plurality of syringes, at least two of the tips of syringes may be connected using multi way-branched tube.

DESCRIPTION OF SYMBOLS

1a Syringe for Contrast Medium
1b Syringe for Physiological saline Solution
2 Y-Shaped Tube
3a, 3b Piston Holder
4a, 4b Motor
5a, 5b Gear Head
6a, 6b Motor Gear
7a, 7b Screw Gear
8a, 8b Ball Screw
9a, 9b Ball Nut Unit
10 Frame Unit
11 Electromagnetic Brake
12 Disc Brake
13 Disc
14 Pad
15 Ratchet
16 Ratchet Pole
17 Rotary Solenoid
19 Cylinder Portion of Ball Nut Unit
21 Wheel Type Ratchet
22 Worm Reduction Gear
23 Cylindrical Worm
24 Worm Wheel
25 Cylindrical Worm Gear
100 Automatic Injection Device

DETAILED DESCRIPTION OF THE INVENTION

In general, in order to move a piston holder forward and backward, the above-described drive mechanism of the automatic injection device converts the rotational movement of a motor into a linear movement by using a ball screw and the like, as described by reference to FIG. 9. Hence, backward-moving prohibition mechanism can be provided in any portion of a transfer route from the motor to the piston holder. That is, depending on the specific embodiment of the invention, the backward-moving prohibition mechanism can be constituted such that either the rotation is prohibited or the linear movement is prohibited.

Referring to a double head type chemical solution injection device mountable with two syringes, a description will be made below. As shown in FIG. 9, the syringe for a contrast medium is mounted on one side of a head A and the syringe for a physiological saline solution is mounted on the other side of a head B. In the same drawings described below, though only the head at the side of the physiological saline solution (at the side of the head B) will be shown, the head at the side of the contrast medium can be constituted similarly to the head at the side of the contrast medium as shown in FIG. 9. In this case, the head A corresponds to the first head, and the head B corresponds to the second head. The head at the side of the contrast medium may also be provided with the backward-moving prohibition mechanism if necessary.

<Embodiment 1>

Figure 1:
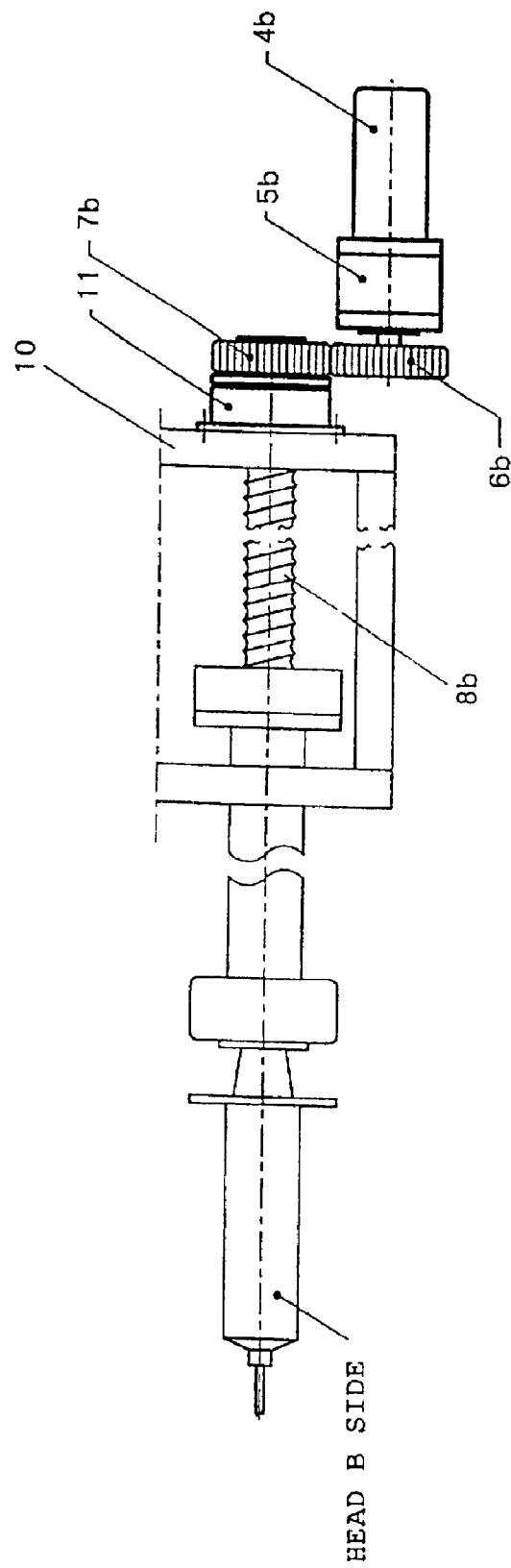
FIG. 1 is a view showing an example of an automatic injection device using an electromagnetic brake.

An example using an electromagnetic brake as backward-moving prohibition mechanism will be described below with reference to FIG. 1.

In this example, the main body of the electromagnetic brake 11 is fixed to a frame unit 10, while the axis (to which a screw gear 7b is fixed) of a ball screw 8b is fixed to an armature side of the electromagnetic brake. Linking and separation between the main body and the armature is performed by controlling the coil inside the electromagnetic brake.

When a syringe piston at the side of the head B is moved forward of backward, the main body and the armature are separated each other (i.e. contact is released), thereby the ball screw 8b can rotate freely by receiving the rotation of a motor 4b. When the electromagnetic brake is turned on, the main body and the armature is linked (i.e. contact is attained), thereby the rotation of the axis of the ball screw 8b is fixed. Hence, if the electromagnetic brake is turned on when the syringe piston at the side of head B is in a stopped state and the syringe piston at the side of the head A is allowed to act, the syringe piston at the side of the head B does not move and there is no risk of sucking the contrast medium.

<Embodiment 2>

Figure 2:
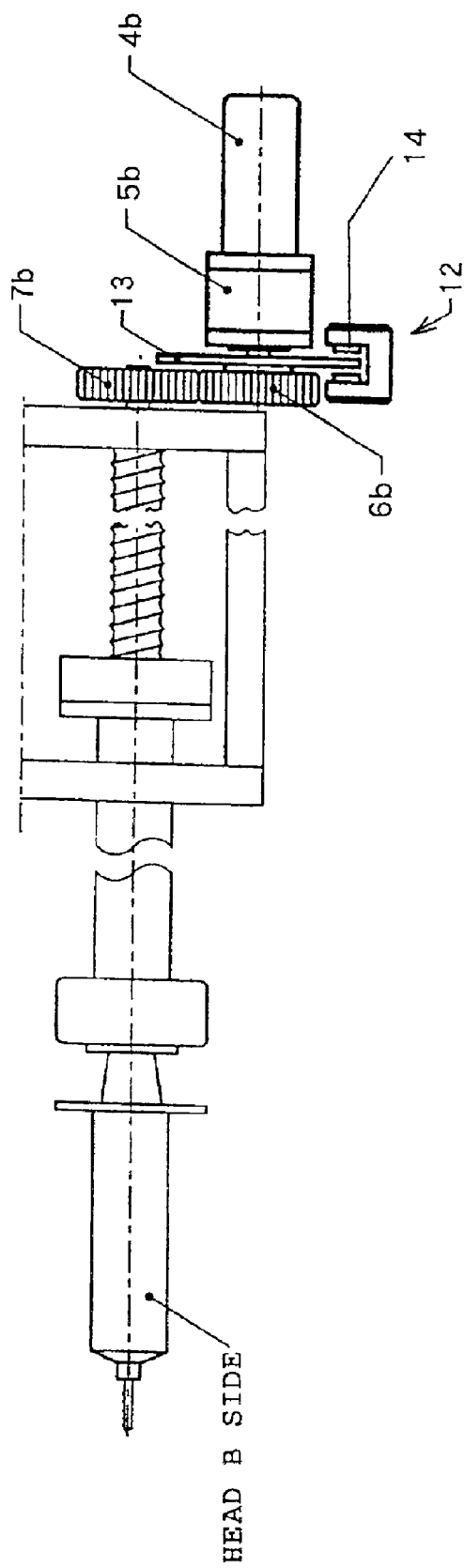
FIG. 2 is a view showing an example of the automatic injection device using a disc brake.

An example using a disc brake as backward-moving prohibition mechanism will be described below with reference to FIG. 2.

The disc brake 12 has a disc 13 and pads 14, which stops the rotation of the disc by holding the disc 13 between the pads 14. When the piston syringe at the head B is moved forward and backward, the space between the disc 13 and the pads 14 is left open so that the motor gear 6b can freely rotate. When the backward-moving of the syringe piston at the head B is desired to be prohibited, the disc 13 may be clamped by the pads 14 by electrically controlling the disc brake.

In this example, though the disc 13 is fixed to the motor gear 6b, it may be fixed to the screw gear 7b or fixed to any place of the axis of rotation.

In the above-described embodiments 1 and 2, though a method of using the brake was described, other types of brakes other than the electromagnetic brake and the disc brake may be used if the movement in the backward direction can be prevented. Moreover, though the embodiments 1 and 2 are constituted such that the rotation is stopped, they may be also constituted such that the linear movement is stopped.

<Embodiment 3>

An example using a ratchet mechanism as the backward-moving prohibition mechanism will be described below with reference to FIG. 3.

Figure 3:
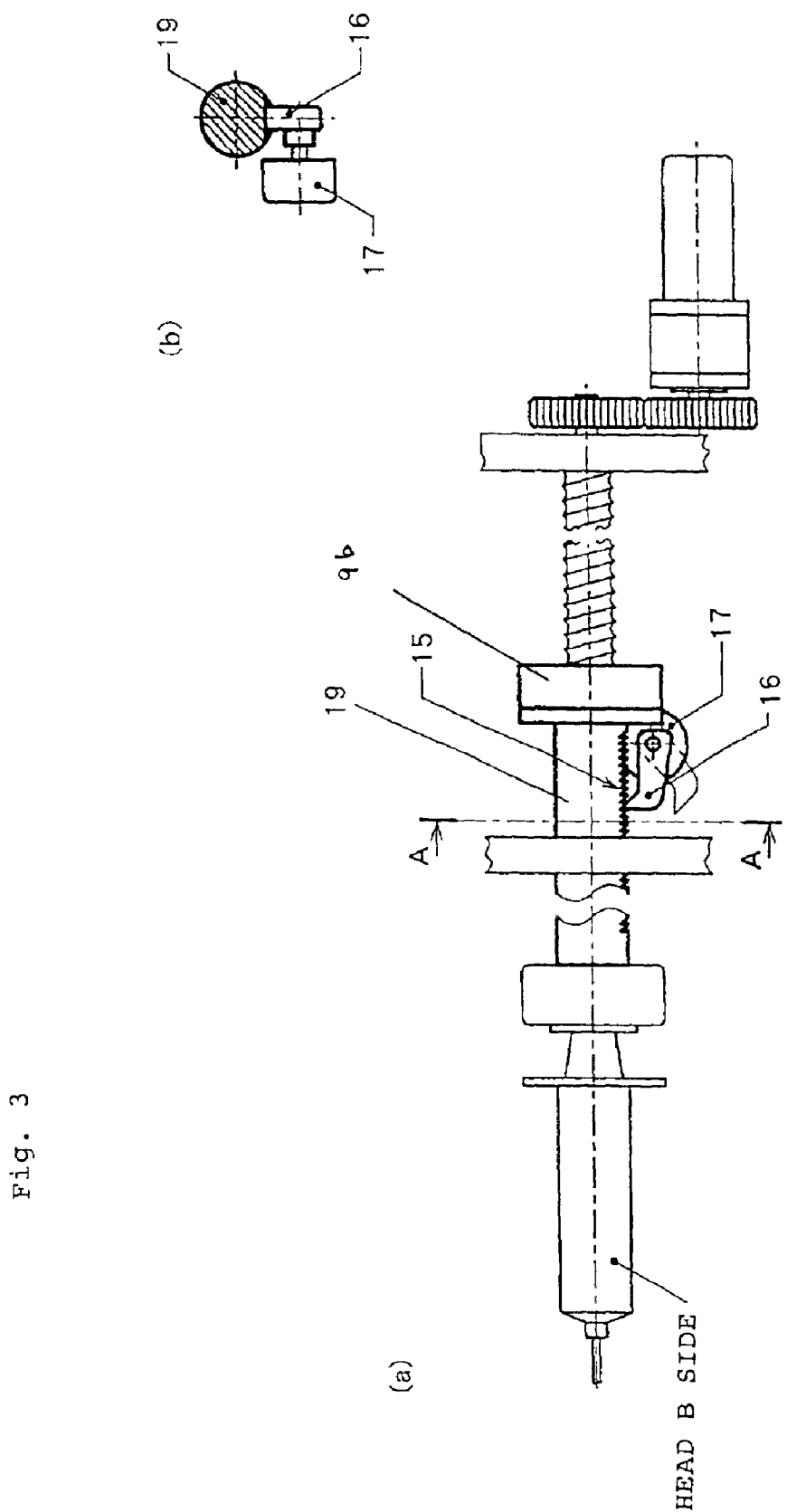
FIG. 3 is a view showing an example of the automatic injection device using a ratchet (linear type).

As shown in FIG. 3(*a*), a ratchet 15 is provided on a cylinder portion 19 of a ball nut unit 9*b* and fitted into a ratchet claw of a ratchet pole 16, making it possible to move forward the syringe piston and prohibit the backward-moving thereof. That is, when at least the motor at the side of the head B is stopped and the ratchet is allowed to engage with the ratchet claw, there is no backward-moving of the syringe piston nor a backward flow. When the syringe piston allows to move backward, a rotary solenoid 17 is electrically controlled so as to rotate the ratchet pole 16, and the engagement of the ratchet and the ratchet claw is released. In FIG. 3(*b*) (cross-sectional view at line A-A in FIG. 3(*a*)), a state of the ratchet being engaged with the ratchet claw and a physical relationship of the rotary solenoid 17 are shown.

The place where the ratchet is provided is not limited to this example, and if it is provided on the member which makes reciprocating movement together with the syringe piston, such construction functions similarly to this example.

<Embodiment 4>

Figure 4:
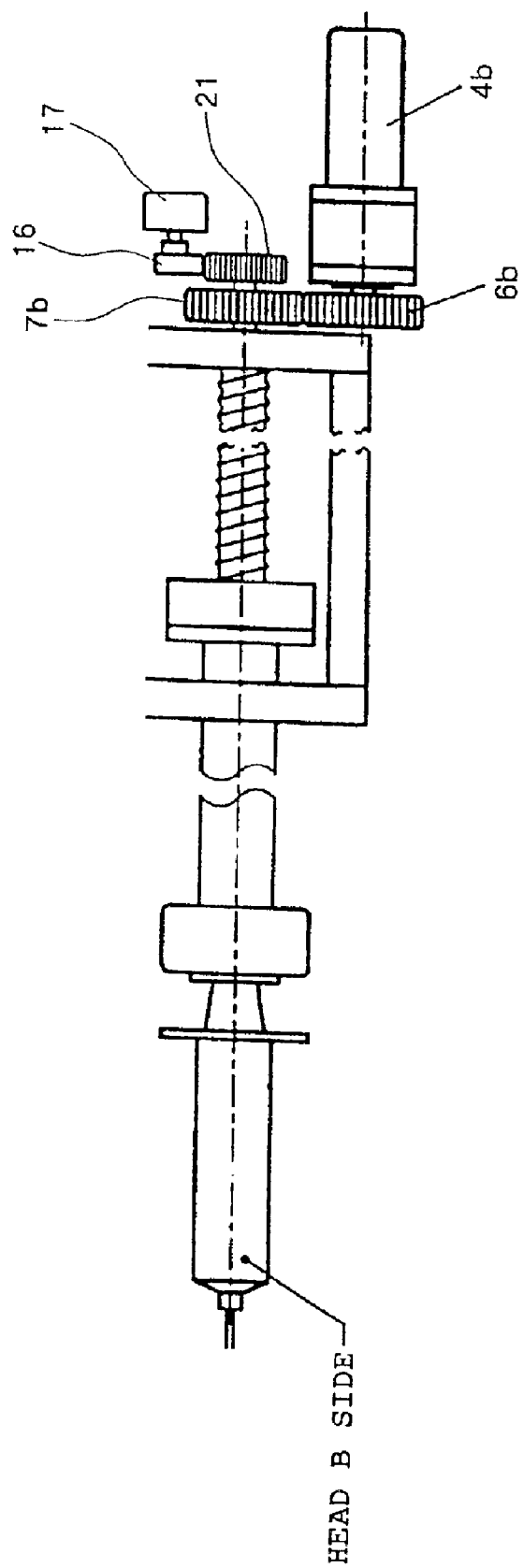
FIG. 4 is a view showing the automatic injection device using a ratchet (wheel type).
Figure 5:
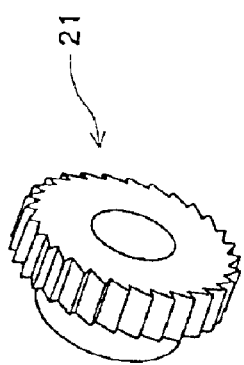
FIG. 5 is an enlarged view of the wheel type ratchet.

In the embodiment 3, the example using the linear type ratchet was shown, but in the embodiment 4, a wheel type ratchet 21 as shown in FIG. 5 is used. As shown in FIG. 4, the wheel type ratchet 21 is fixed to a screw gear 7*b* and is engaged with the ratchet pole 16. Engagement and release of the ratchet is controlled by the rotary solenoid 17.

In this example, the wheel type ratchet is fixed on the axis of a ball screw 8*b* and prevents the ball screw 8*b* from rotating in the backward direction when the syringe piston at the side of the head B is in a stopped state. However, the ratchet may be fixed on the axis of the motor 4*b*.

<Embodiment 5>

Figure 9:
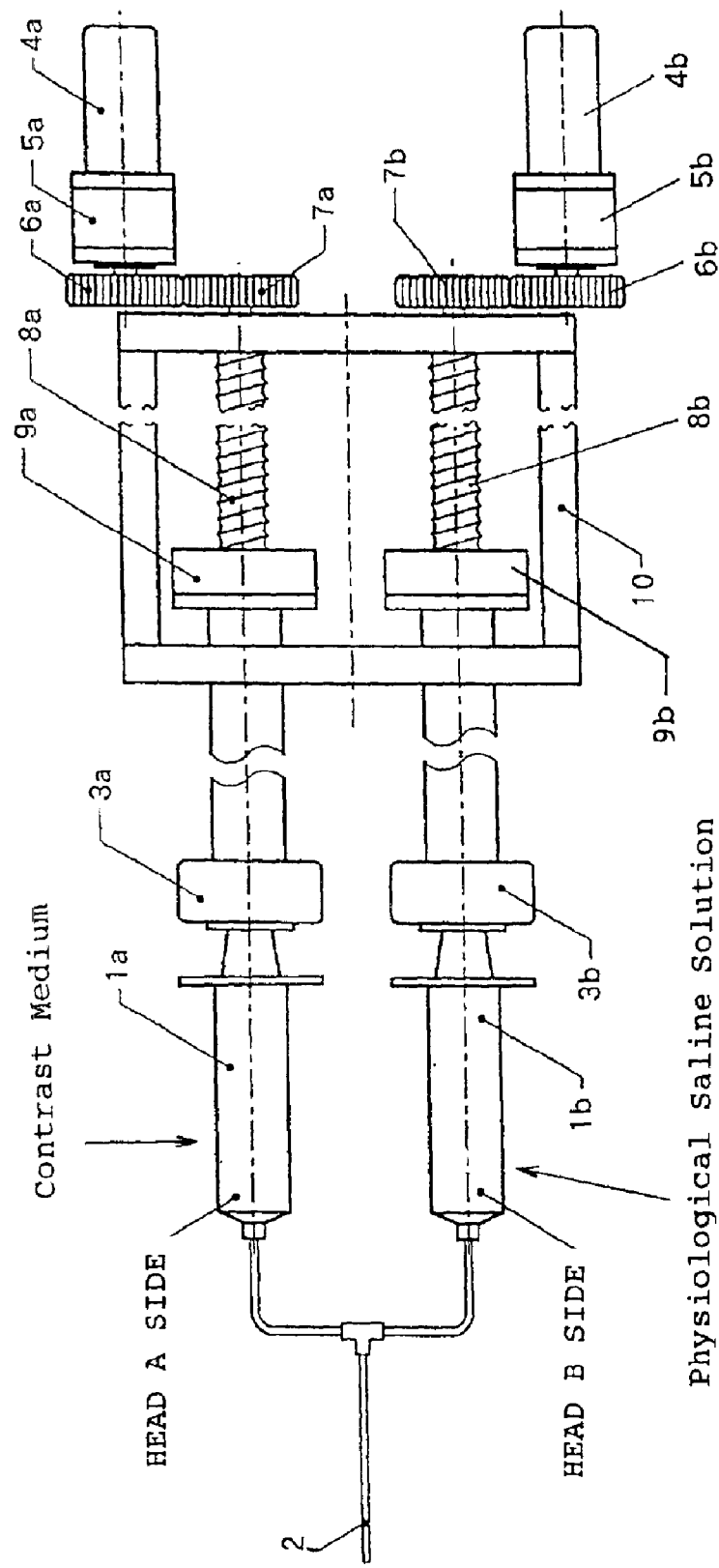
FIG. 9 is a view explaining a drive mechanism of a conventional automatic injection device.

In the devices of the embodiments 1 to 4, examples were shown wherein the rotational transmission route itself from the motor to the ball screw is the same as the conventional route shown in FIG. 9 and provided additionally with the backward-moving prohibition mechanism. In the embodiment 5, the improvement was placed in the rotational transmission route; that is, the transmission is made only in one way from the motor to the ball screw. That is, the transfer route is constituted such that the rotation (both forward and backward directions) of the motor is transferred to the ball screw, on the other hand, even if a force to rotate the ball screw is applied, the force does not incur the rotation of the motor axis.

Figure 6:
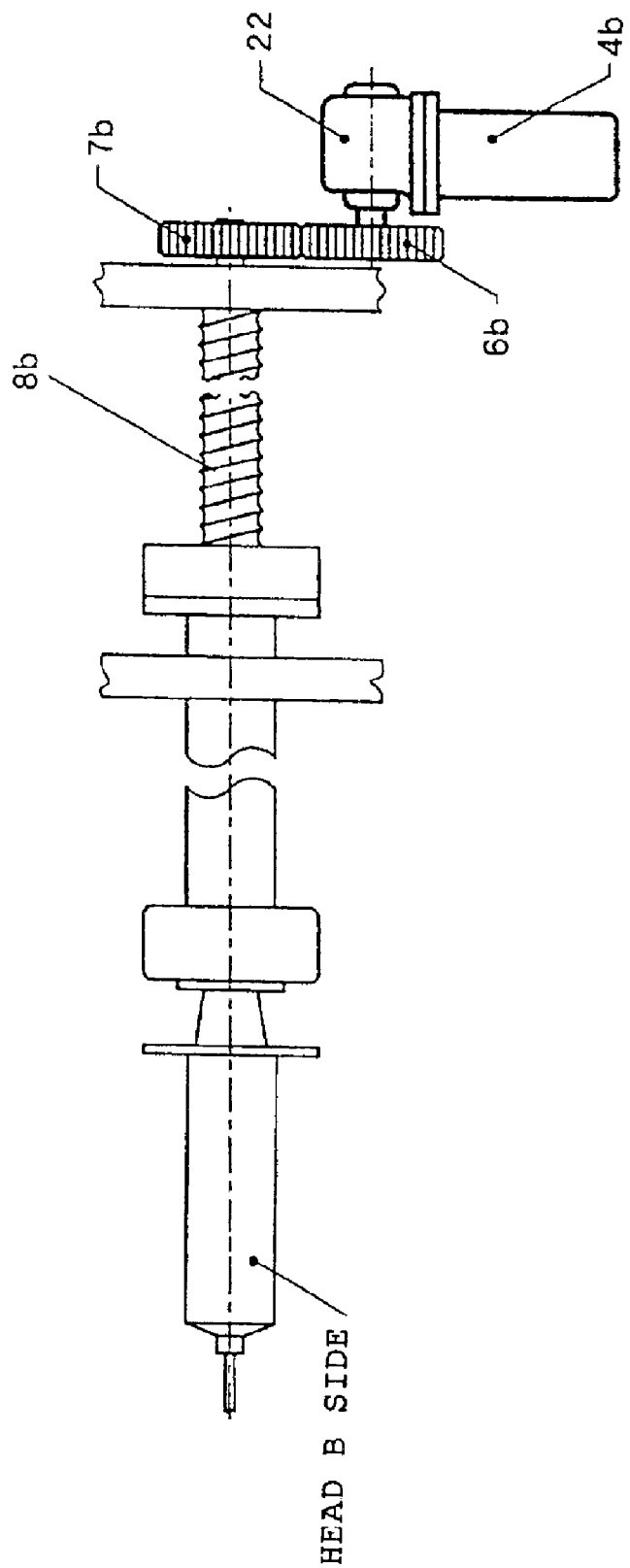
FIG. 6 is a view showing an example of the automatic injection device using a worm reduction gear.
Figure 7:
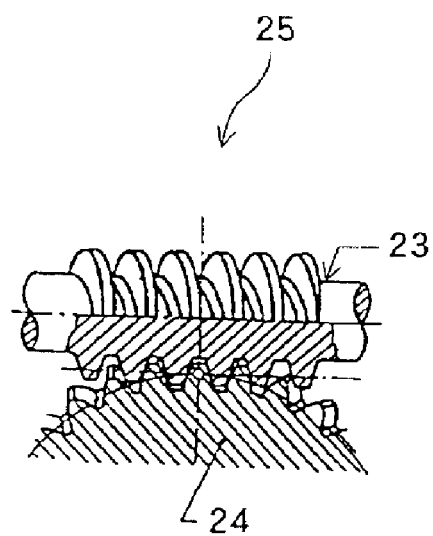
FIG. 7 is an enlarged view of a cylindrical worm gear.
Figure 8:
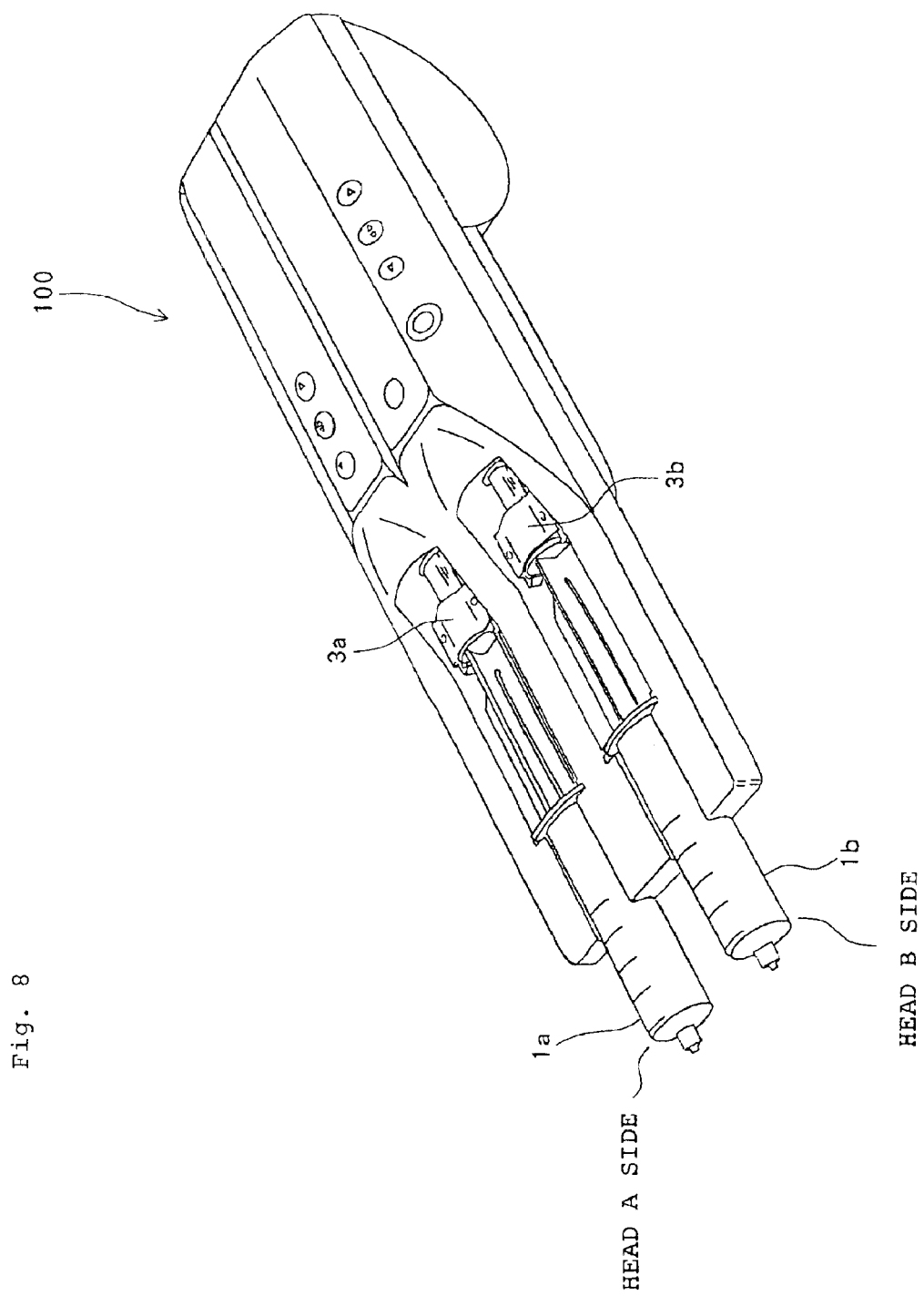
FIG. 8 is a whole view of a double head type automatic injection device.

In an example as shown in FIG. 6, a worm reduction gear 22 using a worm gear is linked to the motor 4*b* and reduces the rotation of the motor, at the same time the axis of motor is arranged such that it is not rotated by the rotational force from the side of the ball screw. Inside the worm reduction gear 22, a cylindrical worm gear 25 comprising a cylindrical worm 23 and a worm wheel 24 is provided as shown in FIG. 7, and the axis of motor is linked to the axis of the cylindrical worm 23, and the central axis of the worm wheel 24 is linked to the axis of the motor gear 6*b*. In this constitution, the rotation of the cylindrical worm 23 is transferred to the worm wheel 24 due to the characteristic of the cylindrical worm gear, but it is not possible to rotate the cylindrical worm 23 even if the wheel worm tries to rotate.

The constitution of the worm gear is not limited to this example. For example, the axis of the worm wheel 24 may be joined to the axis of the ball screw 8*b* so as to be rotated by the cylindrical worm 23.

As described above, according to the present invention, an automatic injection device mountable with a plurality of syringes can be provided wherein, when at least one head is in an injecting state and at least one head is in a stopped state, the backward-moving of the syringe piston of the stopped head is prevented so as to prevent liquid from being undesirably mixed and the injection amount thereof from becoming less accurate.

What is claimed is:

1. An automatic injection device comprising piston holders holding cylinder pistons and plural systems of heads having a drive mechanism for moving the piston holders forward and backward, whereby the device can hold a plurality of syringes and operates injection or suction in each syringe independently, said device comprising a ratchet and a ratchet pole, wherein when the piston holder of a first head is in a forward-moving state then said ratchet pole is engaged with said ratchet whereby the piston holder of a second head is in a stopped state and backward-moving of the second head is prohibited, and wherein the engagement is releasable in order to allow the second head to move in a backward-moving state.

2. The automatic injection device according to claim 1, wherein said drive mechanism has a motor and mechanism for converting the rotation of the motor into a linear movement, and said backward-moving prohibition mechanism prohibits the axis of rotation to rotate in the backward direction.

3. The automatic injection device according to claim 1, wherein said drive mechanism has a motor and mechanism for converting the rotation of the motor into a linear movement, and said backward-moving prohibition mechanism prohibits the linear movement in the backward direction.

4. The automatic injection device according to claim 1, wherein said device is a double head type with the number of systems of heads being two and holds two syringes.

5. The automatic injection device according to claim 4, wherein said device holds a syringe for injecting a contrast medium at the first head and a syringe for injecting a physiological saline solution at the second head.

6. The automatic injection device according to claim 5, wherein the tips of the two syringes are connected to a three way-branched tube.

7. The automatic injection device according to claim 4, wherein the tips of the two syringes are connected to a three way-branched tube.

8. The automatic injection device according to claim 1, wherein said device holds a syringe for injecting a contrast medium and another syringe for injecting a physiological saline solution.

9. An automatic injection device comprising piston holders holding cylinder pistons and plural systems of heads having a drive mechanism for moving the piston holders forward and backward, whereby the device can hold a plurality of syringes and operates injection or suction in each syringe independently, said device comprising an electromagnetic brake, wherein said electromagnetic brake is turned on when the piston holder of a first head is in a forward-moving state and the piston holder of a second head is in a stopped state, whereby backward-moving of the second head is prohibited, and wherein said electromagnetic brake is turned off when the second head is moving state.

10. The automatic injection device according to claim 9, wherein said drive mechanism has a motor and mechanism for converting the rotation of the motor into a linear movement, and said backward-moving prohibition mechanism prohibits the axis of rotation to rotate in the backward direction.

11. The automatic injection device according to claim 9, wherein said drive mechanism has a motor and mechanism for converting the rotation of the motor into a linear movement, and said backward-moving prohibition mechanism prohibits the linear movement in the backward direction.

12. The automatic injection device according to claim 9, wherein said device is a double head type with the number of systems of heads being two and holds two syringes.

13. The automatic injection device according to claim 9, wherein said device holds a syringe for injecting a contrast medium and another syringe for injecting a physiological saline solution.

14. The automatic injection device according to claim 12, wherein said device holds a syringe for injecting a contrast medium at the first head and a syringe for injecting a physiological saline solution at the second head.

15. The automatic injection device according to claim 14, wherein the tips of the two syringes are connected to a three way-branched tube.

16. The automatic injection device according to claim 12, wherein the tips of the two syringes are connected to a three way-branched tube.

* * * * *